US007300407B2

(12) United States Patent
Watrous

(10) Patent No.: US 7,300,407 B2
(45) Date of Patent: Nov. 27, 2007

(54) HANDHELD AUSCULTATORY SCANNER WITH SYNCHRONIZED DISPLAY OF HEART SOUNDS

(75) Inventor: Raymond L. Watrous, Belle Mead, NJ (US)

(73) Assignee: Zargis Medical Corporation, Princeton, NJ (US)

( * ) Notice: Subject to any disclaimer, the term of this patent is extended or adjusted under 35 U.S.C. 154(b) by 95 days.

(21) Appl. No.: 10/984,613

(22) Filed: Nov. 9, 2004

(65) Prior Publication Data

US 2005/0119585 A1 Jun. 2, 2005

Related U.S. Application Data

(60) Provisional application No. 60/518,770, filed on Nov. 10, 2003.

(51) Int. Cl.
*A61B 5/00* (2006.01)

(52) U.S. Cl. ..................................... 600/528
(58) Field of Classification Search ................. 600/528
See application file for complete search history.

(56) References Cited

U.S. PATENT DOCUMENTS

| 4,424,815 A | * | 1/1984 | Kuntz ...................... 600/528 |
| 4,991,581 A | * | 2/1991 | Andries .................... 600/528 |
| 5,010,889 A | * | 4/1991 | Bredesen et al. ........... 600/528 |
| 5,025,809 A | * | 6/1991 | Johnson et al. ............ 600/528 |
| 5,213,108 A |   | 5/1993 | Bredesen et al. |
| 5,218,969 A |   | 6/1993 | Bredsen et al. |
| 5,957,866 A | * | 9/1999 | Shapiro et al. ............. 600/586 |
| 6,520,924 B2 |  | 2/2003 | Lee |
| 6,572,560 B1 |  | 6/2003 | Watrous et al. |
| 6,790,183 B2 |  | 9/2004 | Murphy |
| 2002/0052559 A1 | * | 5/2002 | Watrous ..................... 600/528 |
| 2003/0093002 A1 | * | 5/2003 | Kuo ........................... 600/528 |
| 2003/0176801 A1 |  | 9/2003 | Galen et al. |
| 2003/0176802 A1 |  | 9/2003 | Galen et al. |

FOREIGN PATENT DOCUMENTS

GB 2188732 A * 10/1987

OTHER PUBLICATIONS

Email Site: http://www.cardionics.com, "Pocket Monitor Software For IPAQ", (pp. 1-2), Product Descriptions (pp. 1-24). Copyright 2002.

* cited by examiner

Primary Examiner—Scott M. Getzow
(74) Attorney, Agent, or Firm—RatnerPrestia

(57) ABSTRACT

A handheld auscultatory scanner continuously obtains a heart sound signal from a patient, using a noninvasive passive acoustic sensor, allowing free-form protocol, analysis and display of the heart sound signal on a handheld processing unit in a graphical manner such that a single heart cycle is displayed in a synchronized manner, along with summary results of the processing of the acoustic signal. The results are presented in terms of standard auscultatory findings. The combination of summary findings, heart sound display and audible signal provides a method for assisting in patient screening for heart conditions and for teaching auscultation techniques.

41 Claims, 5 Drawing Sheets

HANDHELD AUSCULTATORY SCANNER WITH SYNCHRONIZED DISPLAY OF HEART SOUNDS

This application is related to and claims the benefit of U.S. Provisional Application No. 60/518,770 entitled HANDHELD AUSCULTATORY SCANNER WITH SYNCHRONIZED DISPLAY OF HEART SOUNDS filed on Nov. 10, 2003, the contents of which are incorporated herein by reference.

FIELD OF THE INVENTION

This invention is in the field of handheld medical sensors, and specifically relates to a handheld auscultatory scanner.

BACKGROUND OF THE INVENTION

Stethoscopes are widely relied upon for acoustic diagnosis in medicine, in particular, for the diagnosis of cardiovascular disease. Stethoscopes, however, have limited functionality, both in design and implementation. For example, the stethoscope itself may only transfer a small fraction of the acoustic signal available at the chest surface to the listener's ears and the stethoscope may filter the cardiac acoustic signal in the process. Electronic stethoscopes may provide gain to improve signal volume, but may still filter the acoustic signal.

Even if the cardiac acoustic signal is transferred faithfully by the stethoscope, proper interpretation of the acoustic signal may be difficult. In particular, with respect to auscultation of the heart, much of the signal energy in many heart sounds may be outside of the range of human hearing. This situation can be compounded by the degradation of the listener's hearing which can be associated with, for example, age and/or exposure to excessive noise. Auscultation relies on correctly determining which of the primary heart sounds correspond to the systolic phase of the heart and which sounds correspond to the diastolic phase of the heart. This is made more difficult when the systolic and diastolic intervals become more equal, such as typically occurs at elevated heart rates.

Learning auscultation is also difficult. Auscultation relies on detecting the correct sequence of brief events that occur close in time, a skill that is often difficult for human listeners. Additionally, diagnostic instructional manuals rely on subjective descriptions of heart sounds, which require practice to appreciate. Furthermore, the practice and teaching of the clinical skill of auscultation of the heart has declined among physicians, partly due to non-reimbursement policies of providers or insurers. Recent studies have concluded that physicians can reliably identify only a small number of standard heart sounds and murmurs. Consequently, serious heart murmurs in many patients may go undetected by physicians.

This decline in auscultation skills has both led to, and been brought about by, a greater reliance on echocardiography. The reliance on echocardiography has weakened the appreciation of auscultation, and the diminished appreciation of auscultation has led to a greater reliance on echocardiography. An improved auscultatory scanner with signal processing capabilities, which is easily used, could greatly assist physicians in the screening process, thereby reducing the number of unnecessary echocardiograms administered.

An additional benefit of the auscultatory scanner would be to recover and re-establish an appreciation of the clinical value of auscultation of the heart, and to provide immediate feedback to the user that would help confirm and refine auscultatory skill, as well as provide a tool that would improve the diagnostic referral process, both in detecting latent murmurs and in correctly deciding not to refer asymptomatic patients with innocent murmurs and no additional associated findings.

SUMMARY OF THE INVENTION

The present invention is embodied in a handheld auscultatory scanner for continuously obtaining a heart sound signal from a patient according to a free-form protocol. The exemplary device uses a means for receiving and digitizing heart sounds. The heart sound signal is analyzed and displayed by a handheld processing unit in a graphical manner such that a single heart cycle is displayed in a synchronized manner, along with summary results of the processing of the acoustic signal.

This invention is contemplated for use in a diagnostic decision support system for auscultation of the heart, such as the system described in MULTI-MODAL CARDIAC DIAGNOSTIC DECISION SUPPORT SYSTEM AND METHOD (U.S. Pat. No. 6,572,560). An exemplary system includes a device to detect the heart sounds, such as a commercially available electronic stethoscope. The heart sounds may desirably be detected from well-defined and standard positions on the chest surface. The detected heart signals are analyzed for features such as heart sounds and murmurs. These features of the recorded heart signals are desirably identified, characterized and described in terms of standard clinical auscultatory findings. In this way, the findings may be used by a physician to make diagnostic and referral decisions, without the need to translate the terms. The free-form protocol and findings by the auscultatory scanner may be used for reinforcement of auscultation training.

BRIEF DESCRIPTION OF THE DRAWINGS

The invention is best understood from the following detailed description when read in connection with the accompanying drawing. It is emphasized that, according to common practice, the various features of the drawing are not to scale. On the contrary, the dimensions of the various features are arbitrarily expanded or reduced for clarity. Included in the drawing are the following figures.

DETAILED DESCRIPTION OF THE INVENTION

Auscultatory Scanner

An exemplary auscultatory scanner according to the present invention may be a hand-held computer that serves as a platform for data acquisition and signal analysis algorithms. This exemplary auscultatory scanner desirably implements real-time, continuous evaluation of heart sounds and murmurs to provide immediate decision support in the diagnosis and evaluation of valvular and congenital heart disease.

Figure 1:
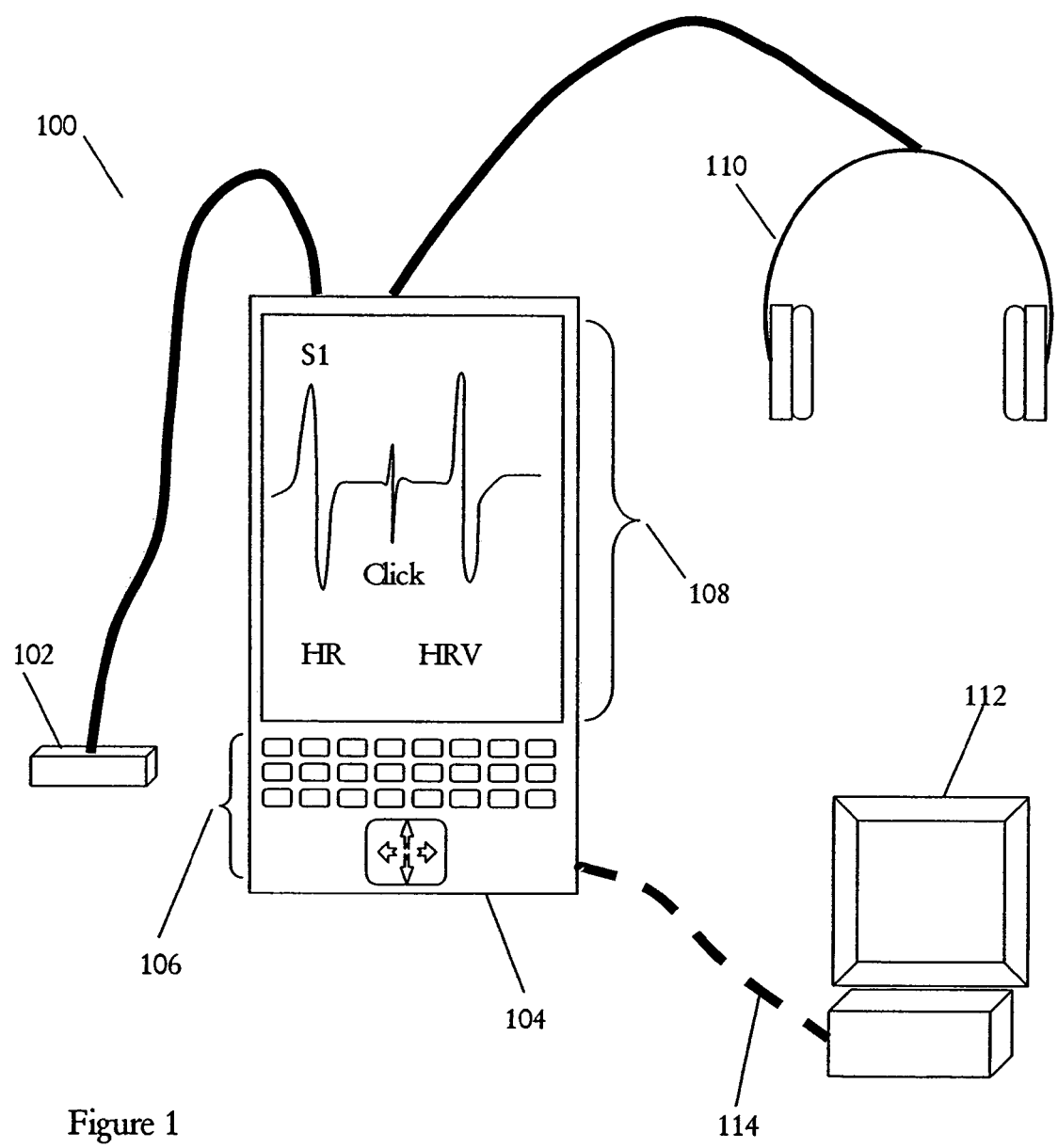
FIG. 1 is a block diagram illustrating an exemplary handheld auscultatory scanner according to the present invention.

Exemplary handheld auscultatory scanner 100, shown in FIG. 1, desirably includes a means for receiving and digitizing heart sounds 102, which is electrically coupled to a handheld computer 104, and headset 110 for simultaneous listening.

The means for receiving and digitizing heart sounds 102 may include a means for coupling cardiac sounds from the chest wall, a transducer for converting the cardiac sounds to an electrical signal and a means for digitizing the electrical signal. The means for receiving and digitizing heart sounds may desirably include analog components, digital signal processing components or both to enhance frequency characteristics of heart sounds. The means for receiving may desirably include analog and or digital signal processing circuitry to amplify heart sounds. The means for receiving may be a passive acoustic sensor. The means for receiving and digitizing heart sounds may desirably be an electronic stethoscope but is not limited to an electronic stethoscope.

Headset 110 may be a separate device electrically coupled to the handheld computer 104 or it may be electrically coupled to means for receiving and digitizing heart sounds. Headset 110 may also desirably include pre-amplification/ signal processing to enhance the frequency characteristics of heart sounds. Means for receiving and digitizing heart sounds 102 and headset 110 may be components of an electronic stethoscope, or they may be separate, electrically coupled, components.

Handheld computer 104 may operate for example according to a Palm OS® or Pocket PC® operating system or may be a special purpose unit including signal processing circuitry and a small display. Handheld computer 104 desirably includes a display 108 and may include an input interface 106. Display 108 may include a touch screen. Handheld computer 104 may also include means for receiving and digitizing heart sounds 102 and pre-amplification/pre-processing circuitry to provide the acoustic signal to the signal processing circuitry.

Handheld computer 104 desirably includes programming or special purpose hardware elements to receive heart sound data where the data is collected according to a free-form protocol to analyze heart sounds and present the annotated heart sounds on display 108. Handheld computer 104 desirably includes memory to store the analyzed heart sounds.

Handheld computer 104 also desirably includes means for entering and storing comments linked to the analyzed heart sounds. This means may include, for example, an input interface 106, a touch screen on display 108 or other suitable data entry facility. A 'hold' feature may also be desirable to allow the display to be frozen for closer review of particular features or heart sounds.

Handheld computer 104 may be coupled, via a physical or logical connection 114, to a general purpose computer 112. Coupling connection 114 between handheld computer 104 and general purpose computer 112 may be an electronic, infrared, wireless or other suitable connection. General purpose computer 112 desirably includes memory, storage capability, signal processing and display capability. In this embodiment the analyzed heart sounds recorded on handheld computer 104 may be transmitted to general purpose computer 112 for storing and later reviewing. General purpose computer 112 may be further configured to analyze the recorded heart sounds transmitted from exemplary auscultation scanner.

Another exemplary embodiment of the present invention is a handheld auscultatory scanner including a replay feature. In this exemplary embodiment, the cardiac acoustic signal data is recorded as it is received by the general-purpose handheld computer. At any point in the process, the user can initiate a replay feature that replays a single previously recorded heartbeat, with a selectable option of a slower playback, suitably processed to maintain the same pitch/frequency content of the audio signal. Desirably, graphical versions of the recorded heart sounds may also be transmitted to a printer, or base-station for uploading to a central server.

Figure 2:
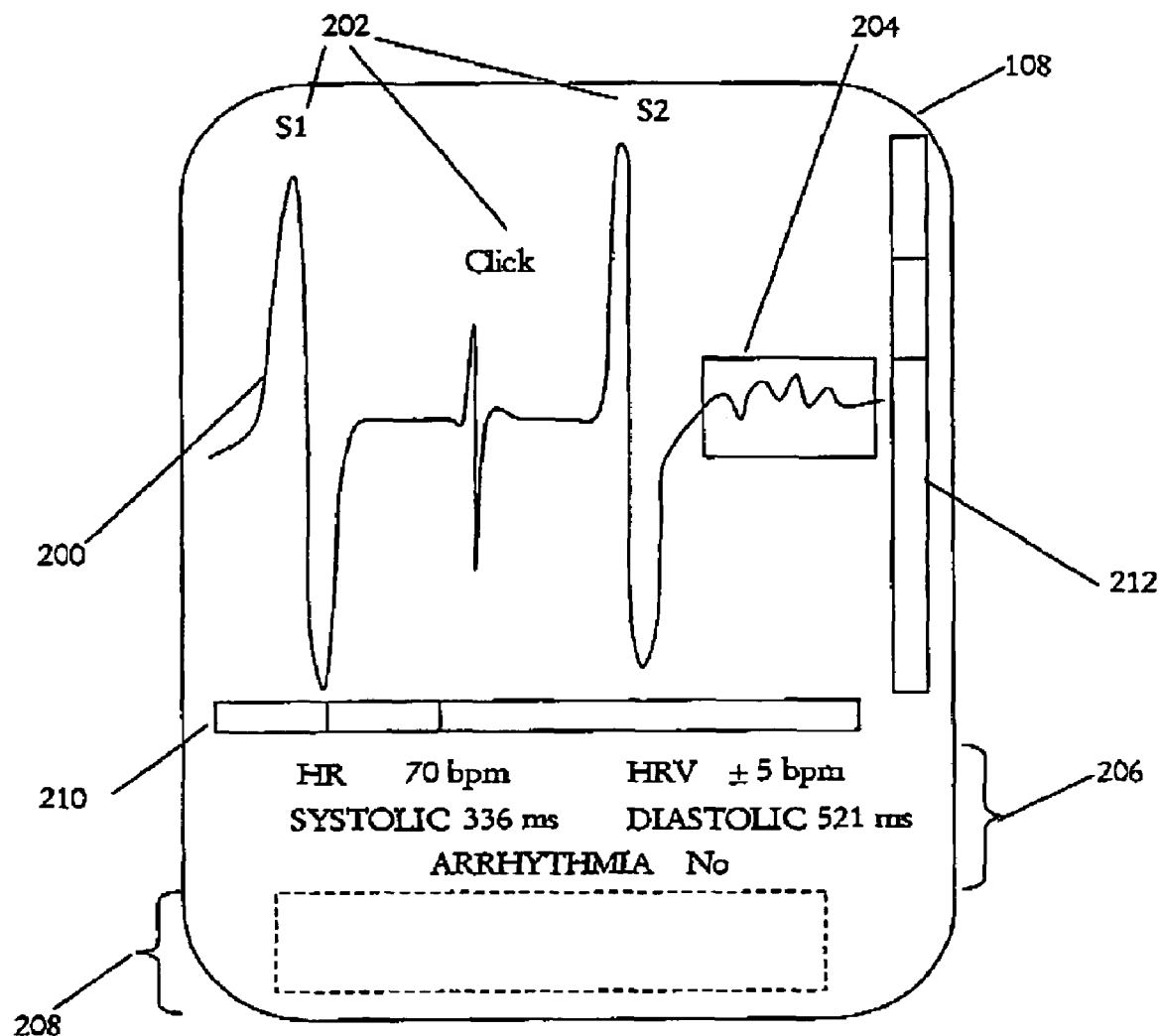
FIG. 2 is a block diagram illustrating an exemplary handheld auscultatory scanner display of FIG. 1 according to the present invention.

FIG. 2 is an exemplary view of components that may be included in the display 108 of the handheld auscultatory scanner. A single heart beat 200 of the cardiac acoustic signal is shown graphically, as well as symbols representing each of the analyzed, found heart sounds 202 and 204. Exemplary hemodynamic parameters 206 are textually shown. A location for entering and displaying comments 208 may also be included. The exemplary locations of components on display 108 are not meant to be limiting. Other desirable information, such as frequency spectrum, murmur intensity and other information may be included or placed on display 108 in a suitable manner.

Heart sounds detected by the analysis algorithms, e.g. S1, S2, S3, S4, ejection sounds, mid-systolic click, opening snap and pericardial knock are desirably annotated by labels 202 at corresponding points on the display 108 of the handheld computer. The labels desirably correspond to standard auscultatory language familiar to the physician.

Murmurs detected by the analysis algorithm are desirably annotated and may also be highlighted, such as, by a semi-transparent box 204 providing the approximate time-amplitude contour of the murmur. These exemplary annotations provide a graphical presentation of the analysis results and may be used to confirm the accuracy of the analysis and the summary clinical findings.

Certain hemodynamic parameters 206 derived from the acoustic signals, such as heart rate (HR), heart rate variability (HRV), systolic/diastolic durations may also be presented in numerical form, with mean/variance values, along with an indication of the presence of any irregularity in heart rhythm (arrhythmia).

Desirably, the graphical display of each heart sound 200 may be synchronized to a preselected heart sound event, for example S1, and may be produced in real time. Additionally, the display may be scaled so that the displayed window is approximately one heart beat wide. Thus, display 108 is typically updated from one heart beat to the next, and displays only sounds from the most recent heart beat. This allows the user to monitor the heart sounds for consistency, variability with respiration, or other beat to beat phenomena.

Graphically displayed single heart beat 200 may also be aligned along the left side of display 108. In this exemplary embodiment, each beat is displayed as it is detected and analyzed and the display may be synchronized based on the detection of the first heart sound (S1), or by autocorrelation analysis, feature extraction and/or probabilistic sequence modeling.

Display 108 may include controls 210 for horizontal scrolling to increase or decrease the scale along the time axis and allow review of specific heart sound details. Horizontal scrolling controls 210 may also include the capability of scrolling along several annotated heart beats 200. The display may also include controls 212 for vertical scrolling to increase or decrease the amplitude of heart beat 200 and allow further review of specific heart sounds. Display 108 may include horizontal scrolling 210, vertical scrolling 212 or their combination. Display 108 may also include other means to review and emphasize displayed heart beat 200.

Auscultatory Screening

The exemplary handheld auscultatory scanner 100 does not keep track of recording length, posture, auscultation site, respiratory cycle or any other maneuvers. The recording protocol is a sequence of steps as desired by the physician whereby the physician may keep mental track of the sequence and results. The physician may have a 'typical' protocol already designed for auscultatory screening. The handheld auscultatory scanner does not hinder the physician by forcing her to follow a fixed format. However, a fixed protocol may be implemented if desired.

Figure 3:
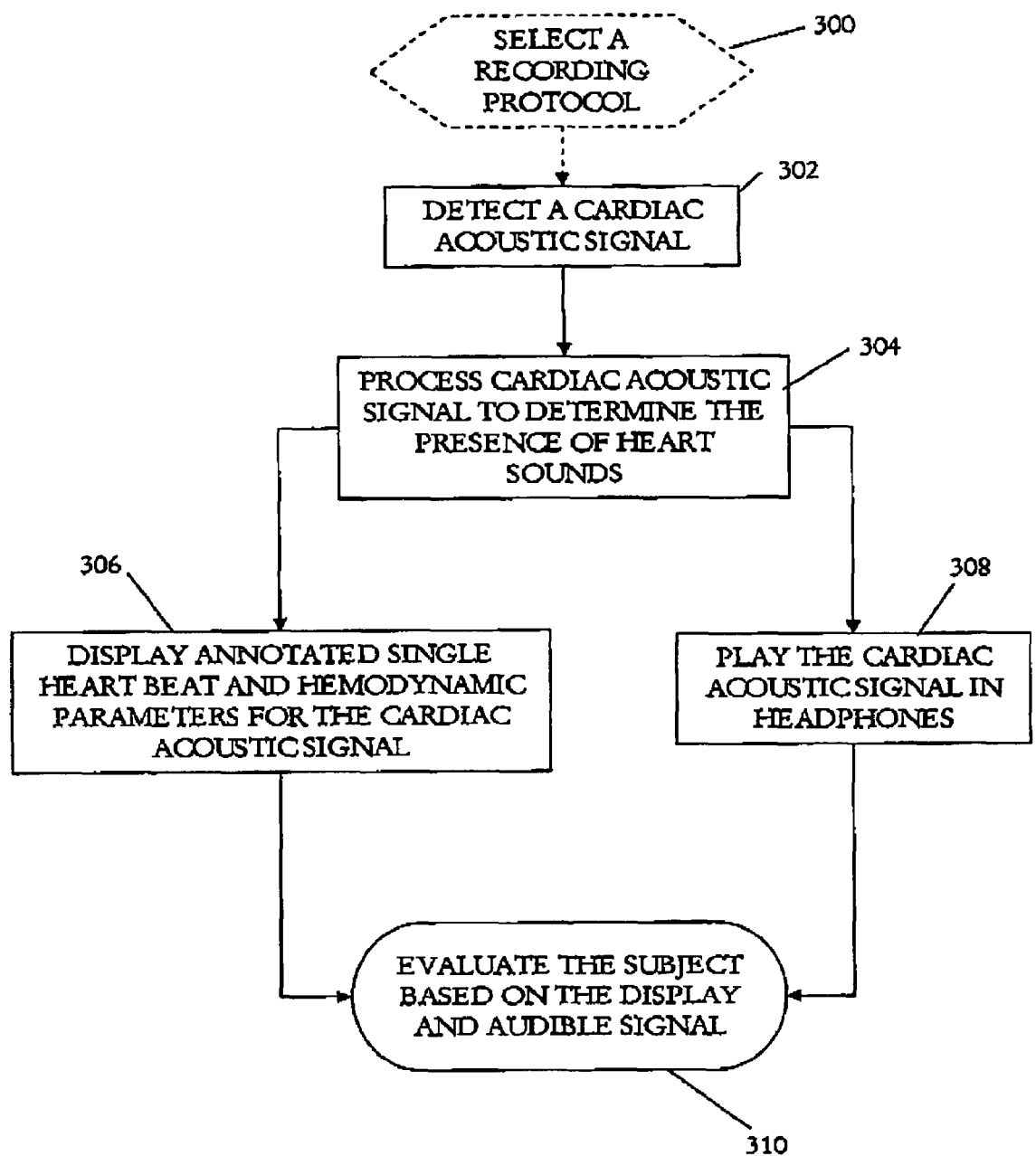
FIG. 3 is a flowchart illustrating an exemplary method of use of the exemplary handheld auscultatory scanner of FIG. 1 for patient screening.

FIG. 3 is a flowchart showing an exemplary method of performing auscultatory screening of a subject according to the present invention. The method begins with the user optionally selecting a recording protocol, step 300. The recording protocol is optional in that the physician may auscultate the patient in a manner of her choosing as described above. A cardiac acoustic signal is then detected by a means for receiving and digitizing heart sounds 102 from the subject, step 302.

The detected cardiac acoustic signal is processed to determine if one or more heart sounds from a predetermined set of heart sounds are present in the cardiac acoustic signal, step 304. An auscultatory analysis program instructs the general-purpose handheld computer. This auscultatory analysis program may be the same as the analysis program disclosed in MULTI-MODAL CARDIAC DIAGNOSTIC DECISION SUPPORT SYSTEM AND METHOD (U.S. Pat. No. 6,572,560). The analysis program continuously scans the audio input, analyzes the heart sounds, detecting clinically significant heart sounds and murmurs, and provides a display of the analysis results. The analysis results desirably include a single heart cycle and summary results of the processing of the acoustic signal.

The results of the analysis of the heart sounds are desirably presented in summary form in terms of standard auscultatory results: for example, late-systolic murmur of grade III, mid-systolic click, loud S2 with wide, fixed splitting, etc. The use of familiar terms in the summary auscultatory findings enables the physician to more easily integrate the results of the heart sound analysis with other patient information. Analysis results may be obtained and/or displayed on a cumulative basis across a number of heart beats or on a beat by beat basis. The results of the analysis of the heart sounds are shown on exemplary display 108, step 306 as a single annotated heart beat with computed hemodynamic parameters.

Desirably, an audible signal corresponding to the cardiac acoustic signal is produced in headset 110, step 308. The audible signal may include a replay feature that replays a single previously recorded heartbeat, with a selectable option of a slower playback, suitably processed to maintain the same pitch/frequency content. An exemplary method may be found in published U.S. Patent Publication No. 2004/0122662 A1.

Desirably, this audible sound is produced contemporaneously with the display of heart sound information described above with reference to step 306. The simultaneous audible sound and displayed information allow the user to easily correlate the sounds heard with the displayed information, thereby increasing diagnostic certainty, step 310. It is contemplated that this simultaneous auditory and visual information may also assist to train physicians in auscultatory techniques.

Figure 4:
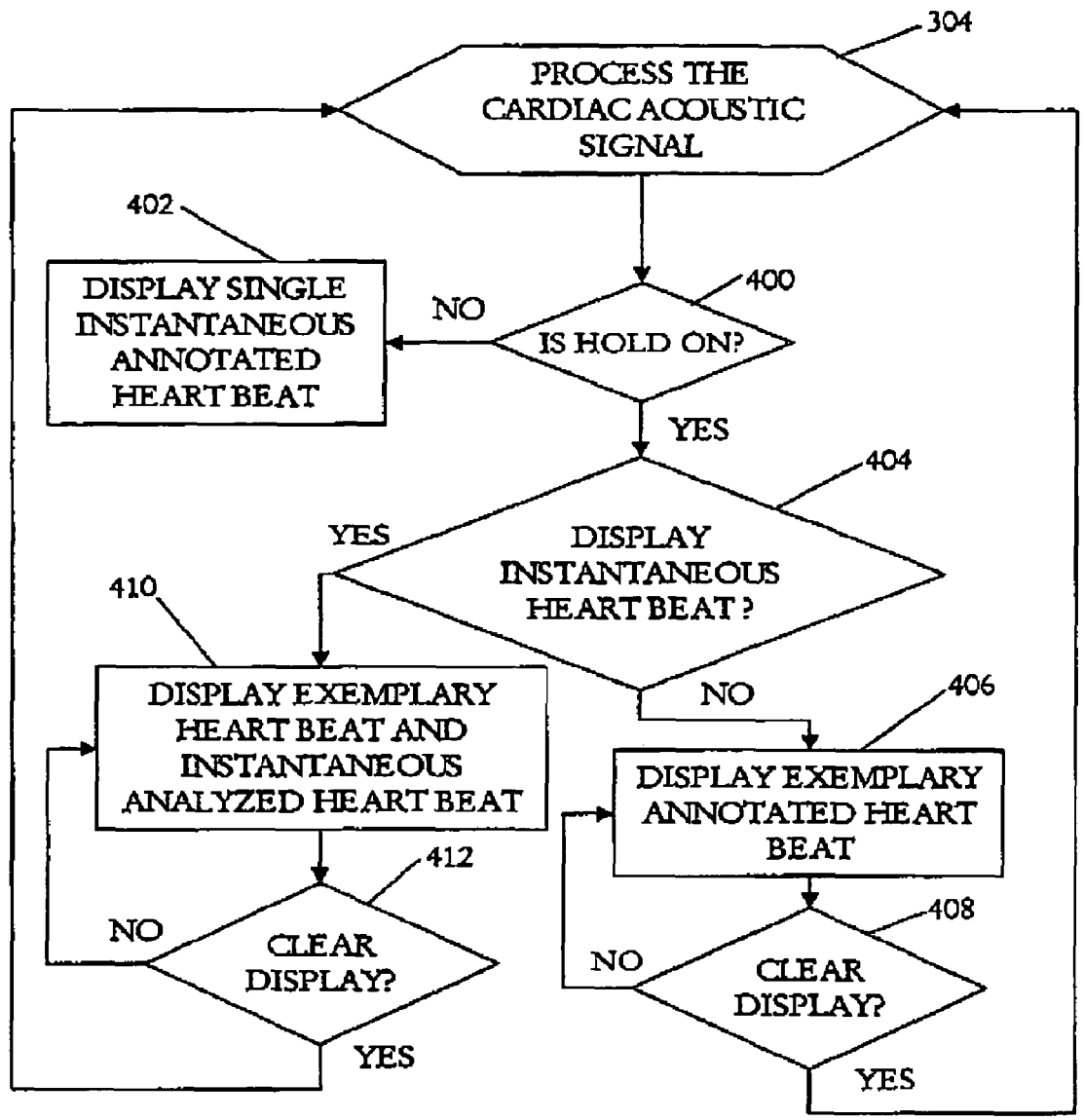
FIG. 4 is a flowchart illustrating exemplary display of annotated heart beat options of the display of FIG. 2.

Graphical display of a single heart beat, step 306, desirably includes options for holding a single heart beat on display 108. FIG. 4 is a flowchart showing an exemplary method of selecting annotated heart beat display options. Concurrently with signal processing of the cardiac acoustic signal, step 304, the user has the option of holding the current heart beat, step 400.

If the user does not want to hold the current heart beat on display 108, the display 108 will show every new heart beat as it is analyzed, step 402. If the user desires to examine the selected heart beat for a longer time, she may choose, step 404, to hold the selected heart beat on the display by itself, step 406 or display the held heart beat concurrently with the instantaneously analyzed heart beat, step 410.

Step 406 allows the physician to further review a selected annotated heart beat. Comments may desirably be added to the held heart beat. The held heart beat and any comments may be stored for later review or transfer to a general purpose computer 112.

Step 410 allows a comparison of changes in the annotated heart beat. Thus the physician can desirably compare heart sounds resulting from, for example, different auscultation sites, postural changes, pharmacological changes, etc. The held heart beat may desirably be displayed in a different color (not shown) or highlighted in some manner (not shown) to emphasize differences in the held and instantaneously analyzed heart beat. The held heart beat may desirably replay the heart sounds through headset 110 with a selectable option of a slower playback, suitably processed to maintain approximately the same pitch/frequency content.

Both steps 406 and 410 allow the user to clear the display 108 of the held and any instantaneous heart beats 200, steps 408 and 412, respectively. The display is then in the state of step 304 and the annotated heart beat graphical display may again be adjusted with any of the options described above.

Auscultation Training

Figure 5:
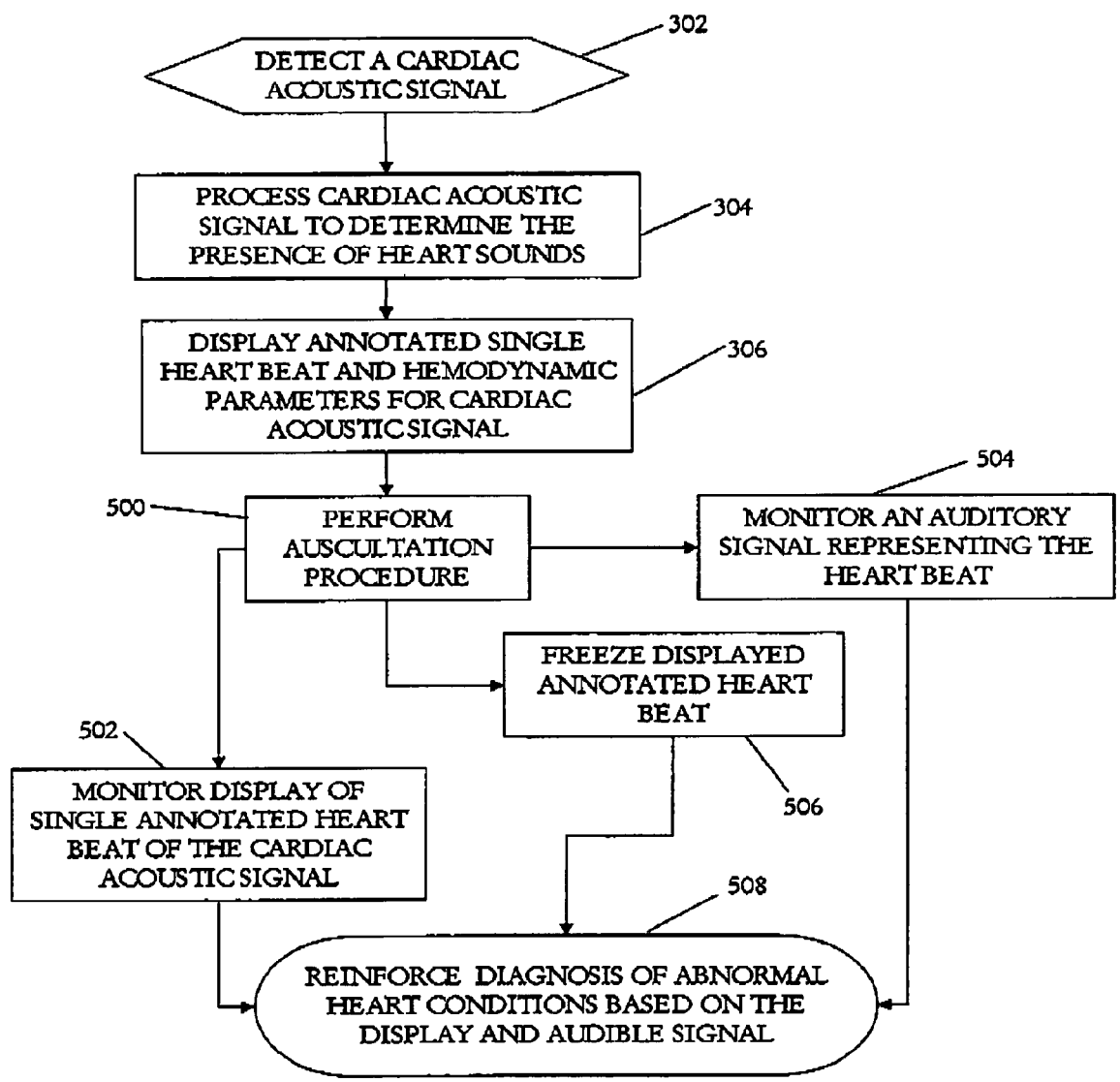
FIG. 5 is a flowchart illustrating an exemplary method of use of the exemplary handheld auscultatory scanner of FIG. 1 for auscultation training.

FIG. 5 is a flowchart showing an exemplary method of training physicians in auscultation techniques. The method begins with the detection of a cardiac signal by the means for receiving and digitizing heart sounds 102 (shown in FIG. 1), step 302. The detected cardiac signal is signal processed in real-time as described above to determine the presence of heart sounds, step 304. As signal processing results are obtained, a single annotated heart beat is displayed, step 306.

A free-form auscultation procedure is performed, step 500. The user is not prompted to follow or record a fixed protocol. There are no requirements for choosing recording duration, auscultation site placement, or posture. The user may desirably follow standard auscultation procedures such as, "inching", sensor pressure changes, postural changes, pharmacological changes, exercise changes, Valsalva maneuver, transient arterial occlusion, auscultation with respiratory cycle or other maneuvers that the physician or instructor desire to practice.

During the free-form auscultation procedure, step 500, the physician may monitor the display of the annotated heart beat and hemodynamic parameters, step 502 concurrently with monitoring an auditory representation of the heart beat, step 504.

As described above, the physician may also freeze the display to a desired annotated heart beat, step 506. The physician may want to further examine a heart beat or may wish to compare a heart beat against an instantaneous heart beat, such as to compare the effect of postural changes on a heart murmur. The physician may further want to replay a single previously recorded heartbeat, with a selectable option of a slower playback, suitably processed to maintain the same pitch/frequency content.

The method of performing an auscultation procedure, step 500, while desirably monitoring the annotated heart beat, step 502, freezing the display, step 506, and monitoring the auditory signal, step 504, may all be used to reinforce diagnosis of abnormal heart sounds based upon the display and audible heart sound, step 508.

Auscultatory Protocol

One desirable use of an exemplary scanner of the present invention is in a screening context, in which a primary care physician/clinician is deciding whether a referral to a specialist is indicated. In this context, ease of use may be a more important concern. A physician may use the analyzer to fully document and archive any heart sounds that are considered suspicious. Following the screening procedure, a more complete and rigorous set of tests may be ordered using the screening results to guide the tests. An advantage of the exemplary scanner is that it is quick and relatively simple to use, yet, guided by the expertise of the user, it may prove a powerful diagnostic instrument. Additionally, the exemplary scanner may highlight murmurs that may be inaudible to the user. This helps to avoid possible misdiagnosis by alerting physicians to a subtle murmur. More thorough detection and analysis of such subtle features may then be performed.

In the MULTI-MODAL CARDIAC DIAGNOSTIC DECISION SUPPORT SYSTEM AND METHOD Patent (U.S. Pat. No. 6,572,560), it was disclosed that, due to the absence of clinically practical sensors to indicate the position of the stethoscope on the chest surface, a fixed protocol should be defined and followed during use of the system. Therefore, auscultation in this method was carried out by listening to the heart at a number of specific sites on the chest in a predefined sequence. The predefined sequence could be configured by the user, but the sequence was to be followed for every auscultation session.

An exemplary method of use for a system of the present invention does not use a fixed protocol, and the physician user is allowed make the association between sensor placement on the torso and the auscultatory findings that are derived from the acoustic signals recorded with the sensor in that position based on her experience. This approach allows the user considerable flexibility in sensor placement and in the sequence of sensor placements. This flexibility allows the present invention to support a wider variety of auscultatory techniques, including "inching," and allows the user to listen at each site for a variable length of time. These changes in protocol may be determined by the user based on sounds heard and auscultatory features detected. This same protocol flexibility may allow for postural changes and dynamic maneuvers of the subject to be solicited by the user.

Design Advantages

In comparison with a laptop-based auscultatory diagnostic decision support system with fixed voice-guided protocol, an exemplary scanner of the present invention may realize the following advantages:

1. System is More Portable and thus Usable

Because the auscultatory diagnostic decision support system is desirably deployed on a handheld platform, the device may be readily placed in a lab-coat pocket and conveniently carried from room to room in a hospital or physician's office. The system may, thus, be treated as part of the stethoscope, and may be used a standard part of the usual stethoscopic component of a physical examination.

2. The User Protocol is Simpler

The user does not need to be prompted through a fixed protocol, nor does she need to specify a recording location. The user keeps track of where the stethoscope is sited, and may use her own judgment to interpret the site-specific results.

3. The Data Capture is Simpler

The user may initiate data capture by pressing a button on the handheld computer. This action may be simpler than pressing a key on a laptop, which may be situated inconveniently on a table or cart, depending on the layout of the examining room. If the design of the examination room makes it convenient, the handheld computer may be set on a table or bed during the examination. Additionally, the use of a handheld computer obviates adding a button to the stethoscope to initiate data capture.

4. More Advanced Protocols are Supported

The user may request the patient to change posture or to execute various maneuvers designed to enhance various auscultatory features. The user may keep mental track of these variables rather than have the system do so and may dynamically alter the protocol as desired during the examination to improve diagnostic quality by following a diagnostic protocol directed by the instantaneous results. Moreover, the user is conceptually free to utilize these options without feeling unsupported by a system that can track site, but not posture, for example, or other maneuvers.

5. Respiration Sensing is not Required

Because the exemplary scanner allows the user to observe the heart cycle in real-time, the user may correlate the auscultatory finding with respiratory changes. This obviates the need for a respiration sensor, algorithmic efforts to derive respiration from the acoustic signal, or other respiration synchronous analysis. For example, the user may watch the splitting of the second sound, for example, as the patient breathes in and out.

6. Display Area is Well Matched to Requirements

The required screen display area for display of a single heartbeat is well matched to the display capabilities of standard handheld computers on the market. These standard handheld computers meet the desired size for user-friendly display of multiple heartbeats recorded at multiple sites. For example, standard general-purpose handheld computer, having a screen resolution of 320 pixels, may display approximately 1 pixel per 3 samples for one second of acoustic signal recorded at a 1000 Hz sample rate.

Although the invention has been described as apparatus and a method, it is contemplated that it may be practiced by a handheld computer configured to perform the method by computer program instructions embodied in a computer-readable carrier such as an integrated circuit, a memory card, a magnetic or optical disk or an audio-frequency, radio-frequency or optical carrier wave.

Although the invention is illustrated and described herein with reference to specific embodiments, the invention is not intended to be limited to the details shown. Rather, various modifications may be made in the details within the scope and range of equivalents of the claims and without departing from the invention.

What is claimed:

1. A handheld auscultatory scanner comprising:
means for receiving and digitizing heart sounds; and
a handheld computer coupled to the means for receiving heart sounds and configured to receive heart sound data collected according to a free-form protocol, to analyze heart sounds, to graphically annotate the heart sounds and to display a most recently received and analyzed graphically annotated heart beat exclusive of any other heart beat,
wherein the handheld computer annotates individual features of the heart beat.

2. A handheld auscultatory scanner according to claim 1, wherein the handheld auscultatory scanner is coupled to a general purpose computer for storage of the heart sounds.

3. A handheld auscultatory scanner according to claim 2, wherein the general purpose computer is further configured to analyze the heart sounds.

4. A handheld auscultatory scanner according to claim 1, further comprising a headset for listening to heart sounds, the headset being coupled to the means for receiving or to the handheld computer.

5. A handheld auscultatory scanner according to claim 4, wherein the handheld computer includes a memory for storing a single heart beat and is coupled to the headset for replaying the stored single heart beat.

6. A handheld auscultatory scanner according to claim 5, wherein the playback is longer in duration than the single heart beat without significantly affecting pitch and frequency content of the single heart beat.

7. A handheld auscultatory scanner according to claim 1, wherein the handheld computer includes a memory to store the analyzed heart sounds.

8. A handheld auscultatory scanner according to claim 1, wherein the handheld computer includes an input interface for entering and storing comments linked to the analyzed heart sounds.

9. A handheld auscultatory scanner according to claim 1, wherein the handheld computer includes a control to clear the display of the annotated heart sounds.

10. A handheld auscultatory scanner including a display device, wherein handheld auscultatory scanner is configured to cause the display device to display:
a graphically annotated analyzed current heart beat exclusive of any other heart beat; and
hemodynamic parameters including at least one of: a heart rate variability, an arrhythmia presence, diastolic durations and a diastolic duration variability of the graphically annotated analyzed current heart beat,
wherein individual features of the heart beat are annotated by the graphically annotated analyzed current heart beat.

11. A handheld auscultatory scanner according to claim 10, wherein the graphical annotation of the current heart beat is selected from the group consisting of heart sounds S1, S2, S3, S4, ejection sound, mid-systolic click, opening snap, and pericardial knock and wherein each of the heart sounds is labeled using standard auscultatory language.

12. A handheld auscultatory scanner according to claim 10, wherein the graphical annotation of the current heart beat further includes an annotation of at least one heart murmur which indicates duration and amplitude of the at least one murmur.

13. A handheld auscultatory scanner according to claim 12, wherein the graphical annotation of the at least one heart murmur includes a semi-transparent box that demarcates a portion of the current heart beat corresponding to the at least one heart murmur.

14. A handheld auscultatory scanner according to claim 10, wherein the current heart beat is aligned by a pre-selected heart sound event along one side of the display device including synchronization at least by one of detection of heart sound S1, autocorrelation analysis, and probabilistic sequence modeling.

15. A handheld auscultatory scanner according to claim 10, wherein the annotated current heart beat is analyzed and displayed in real-time wherein the analysis is performed on the current heart beat.

16. A handheld auscultatory scanner according to claim 10, wherein the annotated current heart beat is analyzed and displayed in real-time wherein the analysis is performed on a cumulative basis over a number of heart beats.

17. A handheld auscultatory scanner according to claim 10, wherein the display device includes a hold feature to review the analyzed heart beat.

18. A handheld auscultatory scanner according to claim 10, wherein the current heart beat is scaled horizontally on the display device to emphasize heart sounds.

19. A handheld auscultatory scanner according to claim 10, wherein the current heart beat is scaled vertically on the display device and the display device includes controls to scroll across the current heart beat or several heart beats as the displayed current heart beat.

20. The handheld scanner according to claim 10, wherein the hemodynamic parameters further include a heart rate, a systolic duration and a systolic duration variability.

21. A handheld auscultatory scanner including a display device, wherein the handheld auscultatory scanner is configured to cause the display device to display:
a graphically annotated analyzed current heart beat;
a user-selected exemplary annotated heart beat, the exemplary annotated heart beat being presented differently than the graphically annotated analyzed current heart beat; and
hemodynamic parameters,
wherein:
individual features of the heart beat are annotated by the graphically annotated analyzed current heart beat, and
the graphically annotated analyzed current heart beat and the exemplary annotated heart beat are displayed exclusive of any other heart beat.

22. A method for assisting in patient screening for heart conditions including the steps of:
detecting a cardiac acoustic signal;
signal processing the cardiac acoustic signal to determine if one or more heart sounds is present;
displaying a current heart beat exclusive of any other heart beat of the cardiac acoustic signal;
graphically annotating the displayed cardiac acoustic signal with the found heart sounds; and
displaying hemodynamic parameters for the cardiac acoustic signal,
wherein the step of graphically annotating the displayed cardiac acoustic signal annotates individual features of the current heart beat, and
the step of displaying the hemodynamic parameters includes displaying at least one of a heart rate variability, an arrhythmia presence, diastolic durations and a diastolic duration variability.

23. The method of claim 22, further comprising the step of playing the cardiac acoustic signal in headphones synchronous with the display of the cardiac acoustic signal.

24. The method of claim 22, wherein the step of graphically annotating the displayed cardiac acoustic signal includes selecting heart sounds to be annotated from the group consisting of heart sounds S1, S2, S3, S4, ejection sound, mid-systolic click, opening snap, and pericardial knock and wherein each of the heart sounds is labeled using standard auscultatory language.

25. The method of claim 22, wherein the step of graphically annotating the displayed cardiac acoustic signal further includes annotating at least one heart murmur in the displayed current heart beat to indicate duration and amplitude of the at least one heart murmur.

26. The method of claim 22, wherein the step of displaying the hemodynamic parameters further includes displaying a heart rate, systolic durations and a systolic duration variability.

27. The method of claim 22, wherein the step of displaying the current heart beat further includes freezing the current graphically annotated heart beat as an exemplary heart beat.

28. The method of claim 22, further Including the step of displaying the graphically annotated current heart beat while concurrently viewing differences in the graphically annotated current heart beat results with respect to a patient respiratory cycle,
whereby the step of displaying the graphically annotated current heart beat allows examination of the instantaneous heart beat variation with respiration to screen for heart conditions.

29. A method far assisting in patient screening for heart conditions including the steps of:
detecting a cardiac acoustic signal;
signal processing the cardiac acoustic signal to determine if one or more heart sounds is present;
displaying a current heart beat of the cardiac acoustic signal;
graphically annotating the displayed cardiac acoustic signal with the found heart sounds;
concurrently displaying an exemplary annotated heart beat; and
displaying hemodynamic parameters for the cardiac acoustic signal,
wherein:
the step of graphically annotating the displayed cardiac acoustic signal annotates individual features of the current heart beat, and
the current heart beat and the exemplary annotated heart beat are displayed exclusive of any other heart beat.

30. The method of claim 27, further including the step of replaying the exemplary heart beat as an audio signal.

31. The method of claim 30, further including playing the audio signal over a longer duration than the exemplary heart beat without significantly affecting pitch and frequency content of the exemplary heart beat.

32. The method of claim 29, wherein the steps of displaying the current heart beat and concurrently displaying the exemplary annotated heart beat includes concurrently displaying in a manner allowing differences to be viewed between the current heart beat and the exemplary annotated heart beat for multiple auscultation sites and postures,
whereby the step of displaying the current heart beat and the exemplary annotated heart beat allows examination of the graphically annotated heart beat with variation of auscultation site and with posture to screen for heart conditions.

33. A method of teaching auscultation including the steps of:
a) detecting a cardiac acoustic signal;
b) signal processing the cardiac acoustic signal to determine if one or more heart sounds is present;
c) displaying a graphically annotated current heart beat exclusive of any other heart beat of the cardiac acoustic signal with found heart sounds;
d) repeating steps a), b) and c) according to a free-form auscultation procedure; and
e) monitoring the displayed graphically annotated current heart beat of the cardiac acoustic signal concurrently with monitoring an auditory signal representing the heart beat while performing the free-form auscultation procedure,
wherein the step of displaying the graphically annotated current heart beat annotates individual features of the heart beat.

34. The method of claim 33, wherein the step of displaying the graphically annotated current heart beat further includes freezing a displayed heart beat to compare respective annotated heart beats.

35. The method of claim 33, wherein the step of displaying the graphically annotated current heart beat includes selecting heart sounds to be annotated from the group consisting of heart sounds S1, S2, S3, S4, ejection sound, mid-systolic click, opening snap, and pericardial knock and wherein each of the heart sounds is labeled using standard auscultatory language.

36. The method of claim 33, wherein the step of displaying the graphically annotated current heart beat further includes annotating at least one heart murmur in the displayed single heart beat to indicate duration and amplitude of the at least one heart murmur.

37. The method of claim 33, wherein the step of displaying the graphically annotated current heart beat further includes displaying hemodynamic parameters including displaying at least one of a heart rate, a heart rate variability, an arrhythmia presence, systolic durations, a systolic duration variability, diastolic durations and a diastolic duration variability for the cardiac acoustic signal.

38. The method of claim 33, wherein the free-form auscultation procedure includes at least one of moving the sensor among standard auscultation positions, inching, sensor pressure changes, positional changes, auscultation concurrently with respiration cycle, Valsalva maneuver, exercise changes, pharmacological changes, transient arterial occlusion, murmur examination after a post ventricular beat, murmur examination after a trial fibrillation,
whereby a user is taught to recognize heart conditions based upon at least one of abnormal heart sounds, variation with posture, variation with respiration and murmur intensity found at specific auscultation sites.

39. A computer readable carrier including computer program instructions which cause a handheld computer to perform a method for assisting in patient screening for heart conditions including the steps of:
detecting a cardiac acoustic signal;
signal processing the cardiac acoustic signal to determine if one or more heart sounds is present;
displaying a current heart beat exclusive of any other heart beat of the cardiac acoustic signal;
graphically annotating the displayed cardiac acoustic signal with the found heart sounds; and displaying hemodynamic parameters for the cardiac acoustic signal,
wherein the step of graphically annotating the displayed cardiac acoustic signal annotates individual features of the current heart beat, and
the step of displaying the hemodynamic parameters includes displaying at least one of a heart rate variability, an arrhythmia presence, diastolic durations and a diastolic duration variability.

40. The computer readable carrier of claim 39, further comprising computer program instructions that cause the handheld computer to perform the step of playing the cardiac acoustic signal in headphones synchronous with the display of the cardiac acoustic signal.

41. A computer readable carrier including computer program instructions which cause a handheld computer to perform a method of teaching auscultation including the steps of:

a) detecting a cardiac acoustic signal;
b) signal processing the cardiac acoustic signal to determine if one or more heart sounds is present;
c) displaying a graphically annotated current heart beat exclusive of any other heart beat of the cardiac acoustic signal with found heart sounds;
d) repeating steps a), b) and c) according to a free-form auscultation procedure; and
e) monitoring the displayed graphically annotated current heart beat of the cardiac acoustic signal concurrently with monitoring an auditory signal representing the heart beat while performing the free-form auscultation procedure,
wherein the step of displaying the graphically annotated current heart beat annotates individual features of the heart beat.

* * * * *